United States Patent [19]

Schmid et al.

[11] Patent Number: 5,204,254

[45] Date of Patent: Apr. 20, 1993

[54] MALTOPENTAOSE PRODUCING AMYLASES

[75] Inventors: Gerhard Schmid; Anton Candussio, both of Munich; August Bock, Kaltenberg, all of Fed. Rep. of Germany

[73] Assignee: Consortium fur elektrochemische Industrie GmbH, Munich, Fed. Rep. of Germany

[21] Appl. No.: 706,699

[22] Filed: May 29, 1991

[30] Foreign Application Priority Data

May 31, 1990 [DE] Fed. Rep. of Germany ....... 4017595

[51] Int. Cl.$^5$ .............................................. C12N 9/28
[52] U.S. Cl. ..................................... 435/202; 435/99; 435/101; 435/69.8; 435/71.2; 435/172.3; 435/252.3; 435/252.33; 435/320.1; 536/23.2; 935/10; 935/14; 935/29; 935/48; 935/56; 935/73

[58] Field of Search .......................... 435/202, 99, 101

[56] References Cited

PUBLICATIONS

Patent Abstracts of Japan, Database JAPS/JPO, vol. 12, No. 270(C515), 27.7.88.

European Journal of Biochemistry, vol. 191, 1990, Berlin, DE, pp. 177-185; A. Candussio et al.: "Biochemical and genetic analysis of a maltopentaose-producing amylase from an alkaliphilic Gram-positive bacterium".

Primary Examiner—Robert A. Wax
Assistant Examiner—Rebecca Prouty
Attorney, Agent, or Firm—Collard & Roe

[57] ABSTRACT

A maltopentaose producing amylase, and its derivatives modified by gene manipulation, can be expressed in *E. col*. These amylases facilitate the production of maltopentaose.

2 Claims, 2 Drawing Sheets

MALTOPENTAOSE PRODUCING AMYLASES

BACKGROUND OF THE INVENTION

1. Field of the Invention

The present invention relates to a maltopentaose (G5) producing amylases and derivatives thereof.

2. The Prior Art

Apart from glucose (glucoamylases) and maltone (β-amylases), only very few maltooligosaccharides can be obtained directly in sufficient purity by hydrolysis of starch using amylases. On hydrolysis of starch, as a rule, α-amylases produce mixtures of glucose and lower molecular weight maltooligosaccharides (G2–G9). Purification of individual components from such mixtures is elaborate and costly. However, individual α-amylases have sufficiently high product specificity to enable the industrial production of defined oligosaccharides. To date, 3 G5 forming amylases have been disclosed:

(a) *Bacillus licheniformis:* U.S Pat. No. 4,039,383, issued Aug. 2, 1977; Arch. Biochem. Biophys., 155, 290–298, (1973)

The enzyme from the thermophilic organism *Bacillus licheniformis* has a temperature optimum of 70° C. and is active in a wide pH range of pH 4.0–10.0. Its molecular weight (MW) is 22.5 kDa. The initial products of amylose hydrolysis are long chain maltooligosaccharides (G5-Gn) which are, however, further degraded as the reaction progresses to the main product G5 and, in relatively large amounts, also to G1–G4. U.S. Pat. No. 4,039,383 of Aug. 2, 1977, describes a process for the hydrolysis and solubilization of amylose (a substrate of low solubility in water). The dissolved amylose is then used as substrate for the purified amylase to produce G5. Because of the many byproducts, the mixture of products after the enzyme reaction must be purified by chromatography.

(b) *Bacillus cereus* NY-14: Japanese Patent No. 158,099, of Sep. 13, 1982, Which Corresponds to U.S. Pat. No. 4,591,561, of May 27, 1986; Japanese Patent No. 142,330, of Aug. 3, 1983; Agric. Biol. Chem., 49 (12), 3369–3376, (1985) (ABC)

The indicated citation (ABC) describes the purification and characterization of a 55 kDa amylase from *Bacillus cereus* NY-14, which shows maximal activity at pH 6.0 and 55° C. The enzyme cleaves starch initially into the maltooligosaccharides G3-G8. The long chain sugars are then subsequently degraded to G1–G5. Japanese Patent No. 158,099, of Sep. 13, 1982, which corresponds to U.S. Pat. No. 4,591,561, of May 27, 1986, describes the production of G5 by culturing a Bacillus strain (NY-14 in this case) in a medium which contains a substrate (starch, amylose, etc.) which can be cleaved into maltooligosaccharides by enzymes which are produced by the organism used. In this process, defined oligosaccharides are obtained by filtration of the culture broth and subsequent chromatography. Japanese Patent No. 142,330 of Aug. 3, 1983, describes the G5-specific enzyme from *Bacillus cereus* NY-14. There is a contradiction in the description of the enzyme to the description in ABC, because the stated MW of the enzyme is 90 kDa in the patent, but is 55 kDa in the publication.

(c) *Pseudomonas sp.* KO 8940: Japanese Patent No. 44,069, of Mar. 9, 1984; Japanese Patent No. 44,070 of Mar. 9, 1984; Japanese Patent No. 253786-87 (Div ex 44069-84); Appl. Microbiol. Biotechnol., 25, 137–142, (1986); Agric. Biol. Chem., 54 (1), 147–156, (1990)

The authors of the Appl. Microbiol. Biotechnol. describe primarily the Pseudomonas isolate KO 8940 and the conditions necessary for production of a G5-amylase. The most recent publication [Agric. Biol. Chem. 54 (1), 147–156 (1990)] describes the purification and biochemical characterization of probably this G5-amylase. The amylase from the Pseudomonas isolate KO 8940 is, however, not expressly mentioned. The purified enzyme has a high initial G5-forming activity. Shorter hydrolysis products occur only after prolonged incubation times. Japanese Patent No. 253786-87 describes the enzyme from Pseudomonas KO 8940 and its use for producing G5. According to this Japanese patent, the amylase has an optimum temperature of 45° C. to 55° C. and an optimum pH of pH 6.0–7.0. Its MW is 72.5 kDa.

Japanese Patent No. 44,070 of Mar. 9, 1984, discloses the amylase producer Pseudomonas KO 8940.

To obtain maltopentaose using the known enzymes, either elaborately purified enzymes are used, or the maltopentaose is elaborately purified from the culture substrate.

SUMMARY OF THE INVENTION

The present invention relates to a maltopentaose producing amylase (A-180) from the isolate 163-26 (DSM 5853) and to processes for preparing derivatives of this amylase. The invention further relates to DNA constructs encoding derivatives of the amylase from the isolate 163-26 (DSM 5853).

According to the present invention, bacteria, preferably alkalophilic starch-degrading bacteria, are screened in a known manner for their ability to produce maltopentaose from starch.

Bacteria with this property are characterized, and the amylolytic enzyme or enzymes are purified and biochemically characterized.

In order to be able to prepare relatively large amounts of the enzyme in prokaryotes, preferably *E. coli*, the enzyme encoding gene is cloned in a vector, preferably a plasmid, and sequenced in a known manner. The encoding gene is modified by directed mutagenesis in such a way that in suitable prokaryotes, the excretion of large amounts of the modified protein, which is able to function as amylase, is possible.

In order to achieve this, the structural gene in the plasmid is placed under the control of an inducible promoter, preferably under the control of the lactose inducible tac promoter. This allows extensive, controllable overproduction of the amylase. In order to prevent intracellular degradation of the enzyme and to make it possible to use the enzyme without elaborate isolation processes, it is desirable to have efficient secretion of the enzyme into the culture medium.

In order to achieve this, the coding region for the signal peptide of a secretable enzyme, preferably the signal peptide of CGTase from *Klebsiella oxytoca*, is fused, while retaining the reading frame, to the structural gene of the enzyme. It is possible, for example, by comparing the protein sequence with the sequences of known amylases to estimate what are functionally important enzyme domains and what are protein regions inessential to the function and, consequently, to subject the structural gene to further modifications which, while retaining the product specificity, result in an enhanced enzyme excretion into the culture medium or bring about an increased enzyme stability in the culture medium.

Hence, there is no necessity for purification or concentration of the enzyme from the culture supernatant. The culture supernatant can be used directly for maltopentaose production. It is then possible, by a suitable choice of the reaction conditions, to design processes in which the maltopentaose yield is so high that purification of the maltopentaose is unnecessary. With yields of G5 above 90%, it is possible to dispense with further purification of the maltopentaose. The maltopentaose can be obtained straightforwardly from the hydrolysis mixtures, for example, by spray drying.

Maltopentaose, the main product of the hydrolysis of starch by the amylase according to the invention and derivatives thereof, is currently used in three areas.

The main area of use of G5 at present is in medical diagnosis. Several different processes have been described for the use of maltooligosaccharides in one method, specifically maltopentaose, as substrates for the accurate determination of the amylase concentrations in body fluids such as urine or serum.

The G5-dependent processes are distinguished in that a number of enzymes are used in combination with unmodified G5 as substrate for the amylase determination. Either the enzymes are added to prevent interference of the measurement with glucose or oligosaccharides present endogenously in the sample material, or they are used in the enzymatic determination of the products resulting from the G5 hydrolysis.

Example: Japanese Patent No. 98282-85: J. Clin. Chem. Clin. Biochem. 21, 45–52, (1983)

Furthermore, maltopentaose can be used in pharmacology in two other areas:

Because of their low sweetening power, their good solubility, and the low viscosity of the solutions, maltooligosaccharides can be used as carbohydrate sources in liquid alimentation for infants, elderly people, or recovering patients.

Fatty acids can also be made soluble in water by esterification with G5. Since solutions of such esterified fatty acids are stable, they are used as infusion solutions after addition of mineral salts.

Example: Japanese Patent No. 226,610, of Oct. 11, 1985

The examples describe the isolation of a maltopentaose producing amylase according to this prior art document, its DNA sequence, its modification by gene manipulation, and its expression in E. coli. Also given are examples of starch conversion using the amylase and its genetically engineered modifications.

BRIEF DESCRIPTION OF THE DRAWINGS

Other objects and features of the present invention will become apparent from the following detailed description considered in connection with the accompanying drawings which discloses two embodiments of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION OF PREFERRED EMBODIMENTS

Example 1

Screening for Maltopentaose Producing Alkalophilic Bacteria

Figure 1:
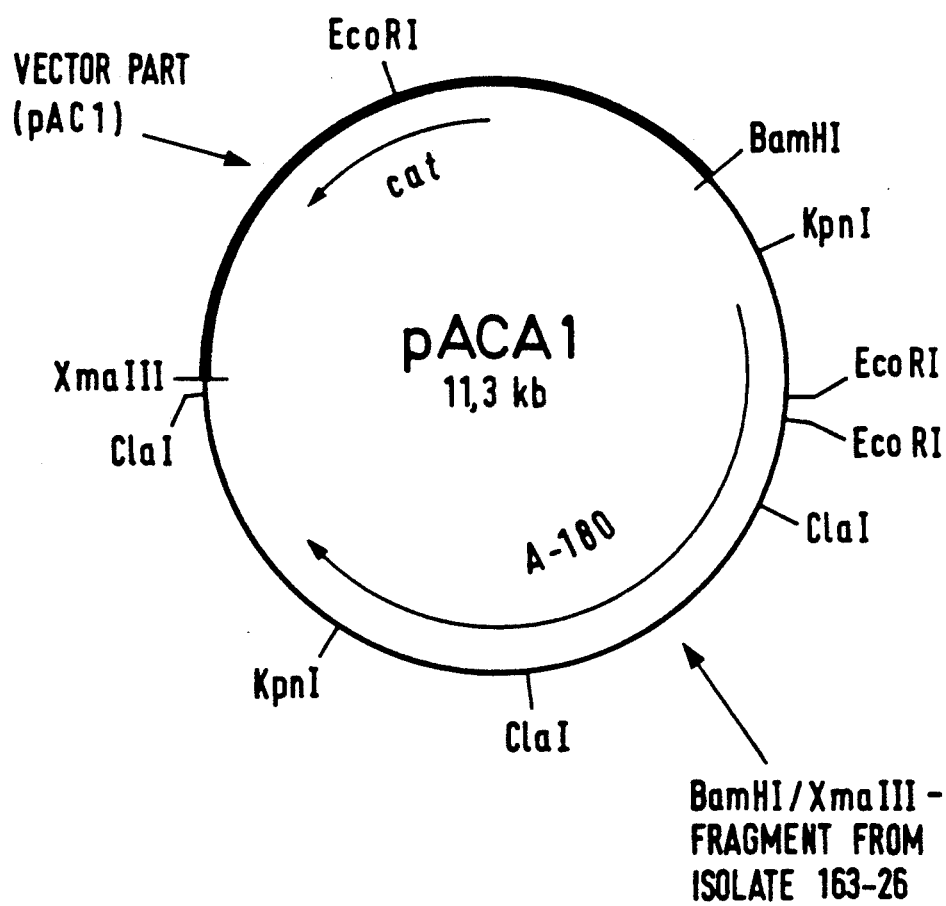
FIG. 1 shows a diagrammatic representation of the plasmid pACA1. A 7.9 kb fragment of chromosomal DNA from the isolate 163-26 was cloned into the BamHI/XmaIII site of the plasmid pAC1 (pACYC184 derivative). The A-180 structural gene contained in the fragment was used to construct the mutants described in the text.

Soil samples from various regions of the earth were collected. 0.1–0.2 g of each sample was suspended in 1 ml of sterile physiological saline in sterile vessels. After sedimentation of the coarse fractions, in each case, 0.1 ml was plated on a starch/agar plate (10 g/l soluble starch; 5 g/l peptone; 5 g/l yeast extract; 1 g/l $KH_2PO_4$; 0.2 g/l $MgSO_4 \times 7H_2O$; 10 g/l $Na_2CO_3$; 15 g/l agar; pH 10.4). The agar plates were incubated at 30° C. for 2–3 days. Colonies of starch-degrading bacteria showed a cloudy halo produced by retrogradation of low molecular weight starch molecules. The colonies were isolated and purified twice on starch/agar plates. This was followed by culturing in 2 ml of liquid medium of the above composition. After incubation at 30° C. for 48 hours, the cells were spun down, and the supernatant was assayed for amylase activity. 200 μl of each supernatant were incubated with 200 μl of a 10% starch solution in 20 mM Tris/Cl pH 9.0; 5 mM $CaCl_2$ at 40° C. for 1–5 hours. The enzyme assay was stopped by adding 600 μl of methanol; the supernatant was centrifuged and then analyzed by HPLC. Out of a large number of isolates, only the strain 163-26 showed the G5-producing enzyme activity.

Example 2

Characterization of the Strain

The following features characterize the alkalophilic isolate 163-26:

| Feature | Isolate 163-26 |
| --- | --- |
| Cell Form: | rod-like, single cells, dimers and short chains |
| Cell Size: | 1–1.6 μm × 0.2–0.3 μm |
| Motility: | almost all the cells are motile in the log. growth phase; almost all the cells are non-motile in the stat. growth phase |
| Endospores: | no endospores occur in any growth phase |
| Growth Parameters: | |
| Temperature: | optimal growth between 30° C. and 37° C. |
| pH: | optimal between pH 8.0 and 9.0 |
| NaCl tolerance: | 8% NaCl still tolerated |
| Quinones: | no quinones occur either aerobically or anaerobically |
| Gram Characteristics: | 30%–70% of the cells are Gram-positive in the log. growth phase |
| Fatty Acid Types: | straight-chain and iso-, anteiso- branched fatty acids |
| Murein Type: | A 1 γ |

| Feature | Isolate 163-26 |
|---|---|
| GC Content: | 41.5 ± 0.5 mol % |

Example 3
Purification and Characterization of the Amylase A-180

The following is an example of a typical purification procedure:

Isolate 163-26 was cultured in 40 l of M3/1 medium (5 g/l Noredux 150B; 5 g/l peptone from casein; 5 g/l yeast extract; 5 g/l NaCl; 3.5 g/l Na$_2$CO$_3$; 1 g/l KH$_2$PO$_4$; 0.2 g/l MgSO$_4$) aerobically at 37° C. for 20 hours. After 20 hours, the culture was rapidly cooled to 4° C. by adding ice. The cells were removed from the culture broth by cross-flow microfiltration in a Millipore filter cassette (pore size 0.2 μm). The proteins in the cell-free culture supernatant were concentrated to a volume of 1 l by ultrafiltration through a Filtron filter cassette (separation limit 10 kDa). The filtrate was brought to 60 percent saturation by the addition of powdered ammonium sulfate. The proteins which were precipitated were collected by centrifugation, dissolved in 50 ml of TC buffer (20 mM Tris/Cl pH 7.2; 5 mM CaCl$_2$), and dialyzed against TC buffer. The amylolytic enzymes in the solution were purified by adsorption to starch. For this purpose, the protein solution after the dialysis was brought to 20% ammonium sulfate saturation, and 3% soluble starch was added. The mixture was stirred at 4° C. for 3 hours and then centrifuged. The precipitate was suspended in half the initial volume of washing buffer (20% saturated with ammonium sulfate, 1M NaCl in TC buffer), stirred at 4° C. for 10 minutes, and centrifuged again. The precipitate resulting from this is suspended in 1 initial volume of elution buffer (3M NaCl; 0.1M maltose in TC buffer) and stirred at 4° C. for 2 hours. The starch is then spun down, and the supernatant is dialyzed against TC buffer. After the dialysis the proteins in the solution are precipitated by adding ammonium sulfate (60% saturation), dissolved in TC buffer and dialyzed again. The resulting solution now contains only the α-amylases A-60 formed by the isolate 163-26 and the maltopentaose producing amylase A-180. The two enzymes can be separated from one another by gel filtrations on a TSK SW3000G (LKB) molecular sieve column.

Characterization of the Amylase A-180

The MW determination by SDS polyacrylamide gel electrophoresis (PAGE) revealed an MW of about 180 kDa for the amylase A-180. The isoelectric point of the purified enzyme was found to be 4.65 by isoelectric focusing. The kinetics of product formation on hydrolysis of starch revealed an initially very high G5 specificity for the amylase A-180. A-180 has a biphasic pH optimum at pH values 6.0 and 8.5. Irreversible inactivation of A-180 takes place only at pH values below 5.5 or above 11.0. The optimal temperature for hydrolysis of starch is 55° C., although the enzyme is slightly unstable at this temperature, so that a temperature of 45° C. is used to produce G5. γ-Cyclodextrin cannot be hydrolyzed by amylase A-180. This result, together with the finding of high G5 specificity, shows that A-180 is an exo-maltopentaohydrolase.

Example 4
Cloning and Sequencing of the A-180 Structural Gene

Cloning—In order to obtain an A-180 specific probe which can be used to identify the structural gene, initially, the N-terminal amino-acid sequence of the purified amylase A-180 was determined by automated Edman degradation (gas phase sequenator). The amino-acid sequence obtained by the sequencing is: (SEQ ID NO: 1)

It was possible to deduce, by reverse translation, from a part of this sequence (SEQ ID NO: 2) a nucleotide sequence which is 17 bases long and must be present in the A-180 structural gene. The exact sequence of this oligonucleotide is: (SEQ ID NO: 3), wherein Y is C or T and N is A, T, C or G.

This oligonucleotide sequence (a 32-fold degenerate 17-mer) was prepared using a DNA synthesizer and radiolabeled with $^{32}$P-γ-ATP. Chromosomal DNA of isolate 163-26 was cut with various restriction enzymes, fractionated by electrophoresis in a 0.8% agarose gel, and transferred to a nylon membrane (Southern blot). It was possible to use the radioactive oligonucleotide mixture in hybridization studies to label a 2.7 kB ClaI fragment which codes for the N-terminal region of A-180. The ClaI fragment was isolated, ligated into the vector pBR322 cut with ClaI, and transformed into E. coli HB 101. Clones which contained the correct insert were identified by hybridization of their plasmid DNA with the radioactive oligonucleotide mixture. It was possible, using the cloned DNA fragment which was now labeled and was used as hybridization probe, to clone the entire A-180 structural gene.

Sequencing—To determine the nucleotide sequence of the A-180 structural gene, overlapping fragments of the gene were sub-cloned into the plasmid pUC19. The sequence of the subclones was determined by the dideoxy chain termination method using universal or internal sequencing primers. A printout of the complete A-180 nucleotide sequence and the derived amino-acid sequence together with the 5' and 3' flanking regions of the gene is represented below. (SEQ ID NO: 4)

The open reading frame which codes for A-180 comprises 5052 nucleotides, corresponding to 1684 amino acids. The derived MW of 186.5 kDa corresponds to the 180 kDa determined by SDS-PAGE.

Example 5
Mutagenesis of the A-180 Structural Gene

Three mutations were necessary to modify the cloned A-180 structural gene in such a way that massive production, coupled with export and proteolytic stability of the G5-specific amylase, takes place in suitable E. coli strains.

In order to obtain massive expression of the A-180 structural gene and, thus, extensive amylase production, which can also be controlled by simple methods (i.e.,induction/repression) the A-180 structural gene was placed under the control of a new promoter. For this, the A-180 structural gene was isolated from the plasmid pACA1 (FIG. 1) and cloned downstream of the tac promoter in the polylinker of the expression plasmid pJF118u (Gene 48, 199-131, 1986 1); a derivative of pKK 223 (the latter is obtainable from Pharmacia, Freiburg). This promoter is repressed by the lacI$^q$ gene product (which is likewise encoded on pJF118u) until inducers such as lactose or analogous compounds, for example, IPTG, are added to the medium.

Although this mutation made massive production of A-180 possible, the recombinant gene product was 100% located in the cytoplasm of *E. coli* and was extensively degraded there.

Figure 2:
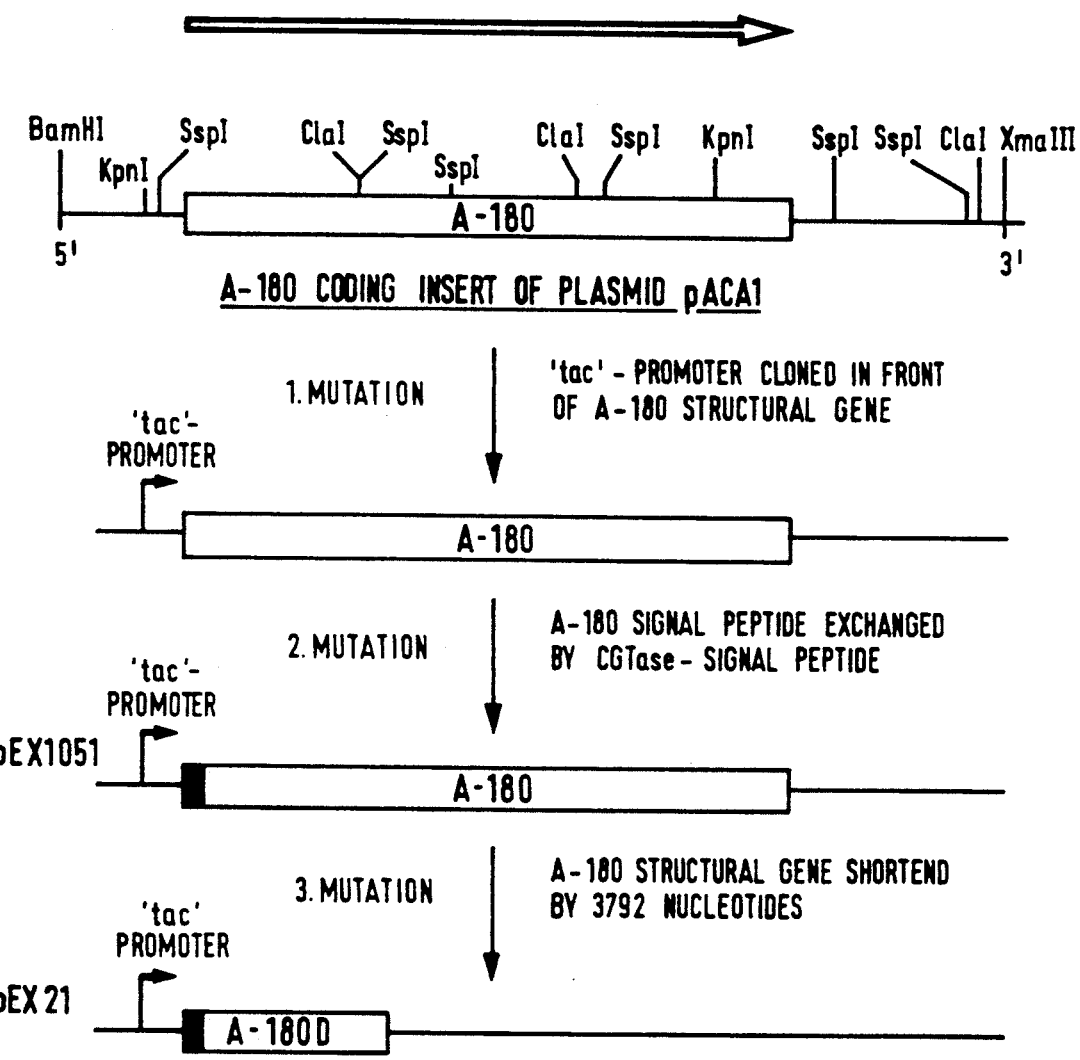
FIG. 2 shows a restriction map of the DNA fragment which was cloned from the isolate 163-26 into the vector pAC1 (pACA1). The diagrammatic representation shows the mutations which resulted in the expression plasmids pEX1051 and pEX21.

In order to achieve export of the produced amylase A-180 into the culture supernatant, the 37 N-terminal amino acids of A-180, which represent the signal peptide necessary for export, were deleted and replaced by the signal peptide of the CGTase from *Klebsiella oxytoca* which is exported in *E. coli* [Gene 47, 269-277, (1986)]. The recombinant plasmid is called pEX1051 (FIG. 2). Expression of the recombinant gene continued via the "tac" promoter. Replacement of the signal peptide resulted in no alteration in the export behavior of A-180. The massively produced enzyme continues to be located in the cytoplasm and is extensively degraded. The G5 specificity is retained, despite the signal peptide exchange.

The third mutation comprised truncating the A-180 structural gene by 3792 nucleotides at the 3' end. The deletion of these nucleotides and the integration of a stop triplet in their place truncates the amylase on the C terminus by exactly 1264 amino acids [plasmid pEX21 (FIG. 2)]. The remaining amylase residue is, like the entire A-180 structural gene, massively expressed under the control of the tac promoter after lactose induction. In contrast to the mutated completed amylase, however, the product which is formed is now exported into the periplasm or the culture supernatant or suitable *E. coli* strains. The exported protein is stable, that is to say it is not degraded, and its enzymic properties are identical in terms of product specificity with those of the complete amylase A-180.

Hence, this gene product meets all the requirements necessary for the production of G5.

Example 6

Expression and Secretion of the Amylase A-180 and of the A-180 Derivative (A-180D) in Various *E. coli* Strains The *E. coli* strains HB101 and WCM100 are used for expression of the amylase A-180 or of the G5-specific 63 kDa A-180 derivative A-180D. HB101 is deposited at the Deutsche Sammlung von Mikroorganismen (DSM 1007), and WCM100 can be obtained by the process described in European Patent Application No. 338,410. It can be replaced for the expression and secretion of the amylases by other strains obtainable by the process disclosed in European Patent Application No. 338,410. The *E. coli* strains contain the expression plasmid pEX1051 for the expression of A-180, and the expression and secretion plasmid pEX21 for the expression of A-180D. 1,000 ml of nutrient medium (10 g/l peptone from casein, 5 g/l yeast extract, 10 g/l NaCl, 5 g/l lactose and 0.1 g/l ampicillin) are inoculated with 20 ml of a preculture of the particular strain (in the same medium) and incubated aerobically at 20° C. (pEX1051) or 25° C. (pEX21). After 48 hours (pEX1051) or 24 hours (pEX21), the cells are harvested by centrifugation of the culture broth.

When the strains HB101/pEX1051 and WCM100/pEX1051 are used, the harvested cells are washed with TC buffer, suspended in 1/200 of the culture volume of TC buffer and lyzed using ultrasound (Sonifier) or pressure (French press). The resulting cell lysates are treated with DNase and then centrifuged at 10,000×g for 10 minutes. After this centrifugation the supernatant (which will hereinafter be referred to as "cytoplasmic fraction") contains the amylase A-180 and can be used directly for starch conversion.

When strain HP101/pEX21 is used, the amylase A-180D, which is located in the periplasm, is extracted from the cells by $CHCl_3$ treatment (Ames et al (1984) J. Bact., 160; 1181-1183). For this, the spun-down cells are suspended in 5 ml of 10 mM Tris/HCl, pH 8.0, mixed with 5 ml of $CHCl_3$ and incubated at room temperature for 15 minutes. The suspension is then diluted with 40 ml of TC buffer and centrifuged at 6,000×g for 20 minutes. After centrifugation, the cell pellet is discarded. The supernatant (periplasmic fraction) contains 60% to 70% of the amylase A-180D formed. Other proteins contained in the plasmic fraction do not inhibit the A-180D activity so that further purification is not necessary.

When strain WCM100/pEX21 is used, the harvested cells are discarded. Under the described conditions, the culture supernatant contains 0.1–0.5 g of the recombinant gene product A-180D, while the inducer lactose has been almost completely consumed by this time. The cell-free culture supernatant can be used directly for starch conversion.

Example 7

Starch Conversion With Maltopentaose Producing Amylases Obtained From Isolate 163-26 or *E. coli*

Example 7.1

Starch Conversion With Amylase A-180 Purified From the Culture Supernatant From Isolate 163-26

Purified amylase A-180 is dissolved to a concentration of 50 μg/ml in TC buffer. A 10% solution of soluble starch in TC buffer is brought to a temperature of 45° C. The two solutions are mixed in the ratio 1:1 and incubated at 45° C. After 1 hour, the reaction is stopped by adding 1.5 parts by volume of methanol. The unhydrolyzed residual starch precipitated by the methanol addition is spun down. The hydrolysis products remaining in the solution can be qualitatively and quantitatively investigated by reversed phase column chromatography. In a typical starch conversion in which 1 ml of enzyme solution and 1 ml of substrate solution have been employed, 18.5% of the starch contained in the mixture was hydrolyzed after 1 hour. The resulting products have the following composition: G5, 82.7%; G4, 6.4%; G3, 4.2%; G2, 3.9%; G1, 2.8%.

Example 7.2

Starch Conversion With Amylase A-180 Contained in the Cytoplasmic Protein Fractions From *E. coli* Cells The cytoplasmic protein fractions from *E. coli* HB101/pEX1051 or *E. coli* WCM100/pEX1051 are prepared as described in Example 6. The concentration of the proteins is adjusted to 2 mg/ml with TC buffer. 35 ml of a 30% Noredux 150B solution (in TC buffer) are equilibrated at 45° C. Noredux 150B is a starch partially hydrolyzed by acid treatment and supplied by Henkel. The substrate is then mixed with 5 ml of the protein solution (2 mg/ml) and incubated at 45° C. 4 ml samples of the mixture are removed after 1, 2, 3 and 4 hours and mixed with 6 ml methanol and are centrifuged. The qualitative and quantitative composition of the soluble products in each supernatant is determined by HPLC analysis. The results of a typical starch conversion with amylase A-180 contained in the cytoplasmic protein fraction of *E. coli* HB101/pEX1051 or *E. coli* WCM100/pEX1051 are shown in the following table:

|  | 1 h | 2 h | 3 h | 4 h |
|---|---|---|---|---|
| Proportion of Substrate Hydrolyzed | 12.1% | 19.9% | 24.95% | 31.1% |
| Product Composition: | | | | |
| Maltopentaose: | 100% | 79% | 72% | 64% |
| Maltotetraose: | 0% | 8.5% | 10.4% | 12.2% |
| Maltotriose: | 0% | 7.5% | 10.4% | 11.6% |
| Maltose: | 0% | 5% | 6.2% | 7.4% |
| Glucose: | 0% | 0% | 1% | 4.8% |

Example 7.3

Starch Conversion With Amylase A-180D Contained in the Periplasmic Fraction of *E. coli* HB101/pEX21

95 ml of 10% Noredux 150B solution are equilibrated at 45° C. The solution is then mixed with 5 ml of periplasmic fraction of *E. coli* HB101/pEX21 (compare Example 6) and incubated at 45° C. After 1 hour, the reaction is stopped by adding 150 ml of methanol. The mixture is centrifuged; the product composition in the supernatant is then determined by HPLC analysis. Under the conditions described, 38.4% of the employed substrate is hydrolyzed after 1 hour. The resulting products have the following composition: G5, 67.7%; G4, 11.1%; G3, 1.7%; G2, 8.7%; G1, 10.8%.

Example 7.4

Starch Conversion With Amylase A-180D Contained in the Culture Supernatant From *E. coli* WCM100/pEX21

75 ml of 10% Noredux 150B solution are equilibrated at 45° C. The solution is then mixed with 25 ml of culture supernatant from *E. coli* WCM100/pEX21 (compare Example 6) and incubated at 45° C. After 1 hour, the reaction is stopped by adding 150 ml of methanol. The mixture is centrifuged; the product composition in the supernatant is then determined by HPLC analysis.

After one hour, there was 15.8% composition of the substrate employed. The product composition was:

| Maltopentaose: | 91.3% |
|---|---|
| Maltotetraose: | 5.4% |
| Maltotriose: | 1.2% |
| Maltose: | 0.9% |
| Glucose: | 0.9% |

While only two embodiments of the present invention have been shown and described, it is to be understood that many changes and modifications ma be made thereunto without departing from the spirit and scope of the invention as defined in the appended claims.

What is claimed is:

1. An isolated and purified maltopentaose producing A-180 amylase protein, which protein has the following properties:
   (a) a molecular weight of 180,000 daltons as measured by SDS polyacrylamide gel electrophoresis;
   (b) a pI of 4.65 as measured by isoelectric focusing;
   (c) is able to hydrolyze a starch solution to produce a product composition comprising greater than 80% maltopentaose;
   (d) is unable to hydrolyze γ-cyclodextrin;
   (e) is thermostable up to 50° C. and;
   (f) is stable within the pH range 5.5–11.0.

2. An amylase which produces maltopentaose obtained by
   (a) placing the gene of the amylase, as set forth in claim 1, under the control of a controllable promoter in a vector;
   (b) replacing the first 111 coding bases of this gene by the DNA sequence of the signal peptide of the CGTase from *Klebsiella oxytoca*;
   (c) deleting the 3792 nucleotides at the 3' end of the amino acid encoding portion of said gene and integrating a stop triplet there; and
   (d) expressing the gene modified in this way in a suitable prokaryote, and secreting the protein thus produced.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
( A ) LENGTH: 25 amino acids
( B ) TYPE: amino acid
( D ) TOPOLOGY: linear ( i i ) MOLECULE TYPE: peptide ( x i ) SEQUENCE DESCRIPTION: SEQ ID NO: 1:

Gln Glu Tyr Arg Glu Leu Asn Gln Leu Glu Asn Lys
1           5             10

Pro Phe Ser Trp Asp Asn Ala Asn Val Tyr Phe Val
    15          20

Leu
25

( 2 ) INFORMATION FOR SEQ ID NO: 2:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( x i ) SEQUENCE DESCRIPTION: SEQ ID NO: 2:

Trp Asp Asn Ala Asn Val
1           5

( 2 ) INFORMATION FOR SEQ ID NO: 3:

( i ) SEQUENCE CHARACTERISTICS:
    ( A ) LENGTH: 17 bases
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO: 3:

TGGGAYAAYG CNAAYGT                17

( 2 ) INFORMATION FOR SEQ ID NO: 4:

( i ) SEQUENCE CHARACTERISTICS:
    ( A ) LENGTH: 5741 bases
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO: 4:

```
GGTACCGCCT ATCTCAGTGT GTGAAAGCTA TGCATCAAAA TACCTACTCC    50

ATGAGCGTTT CTTCAACACG AATCTACTTT ATTTAATATT ATTCATAACG   100

AAACATCAGA AAATATTGTT ATTACCTAAA TTCCTTGTTT TTGTCTTTTA   150

ATGTTGGTCA ATGTTCTATG GTTGTGCTAA TAAAAATGTT AACGCTTTCT   200

CAGGAGGCTA TATGAGAGGG GTGATGTCTG CTAAACAATA AGGATTCATC   250

AACACCATGG TTATAAAAAA TTAAAGATTG AAAGGAGGAA AAGGTA ATG   299
                                                    Met
                                                      1

AAG CAA CAG CTT AAT CGC GTG ATA AGT ATC GTA TTA TGT TTA ATT   344
Lys Gln Gln Leu Asn Arg Val Ile Ser Ile Val Leu Cys Leu Ile
  5              10                 15

GTC ATG CTC TCG GTG TTT GAA AGT ACT ATT ATG TTA TTA CCA GGT   389
Val Met Leu Ser Val Phe Glu Ser Thr Ile Met Leu Leu Pro Gly
 20              25                 30

TCA GTA GAG GTA AAA GGC CAA GAG TAT CGA GAA CTA AAT CAG CTA   434
Ser Val Glu Val Lys Gly Gln Glu Tyr Arg Glu Leu Asn Gln Leu
 35              40                 45

GAA AAT AAA CCT TTT TCA TGG GAT AAT GCA AAC GTT TAC TTT GTG   479
Glu Asn Lys Pro Phe Ser Trp Asp Asn Ala Asn Val Tyr Phe Val
 50              55                 60

TTA ACC GAT CGT TTT TAC AAT GGA AAT ACA AGT AAT GAT AAT TCT   524
Leu Thr Asp Arg Phe Tyr Asn Gly Asn Thr Ser Asn Asp Asn Ser
 65              70                 75

TAT GGG AGA CCG CAA ATA GAT GCT TGG GGT ACA AAC ATT GGT ACT   569
Tyr Gly Arg Pro Gln Ile Asp Ala Trp Gly Thr Asn Ile Gly Thr
 80              85                 90

TTC CAT GGC GGG GAC ATA AAA GGA TTA ACA AAG AAA TTG GAA GAA   614
Phe His Gly Gly Asp Ile Lys Gly Leu Thr Lys Lys Leu Glu Glu
 95             100                105

GGT TAC TTT ACA GAC CTA GGT ACA AAT GCC ATA TGG ATA TCT GCT   659
Gly Tyr Phe Thr Asp Leu Gly Thr Asn Ala Ile Trp Ile Ser Ala
110             115                120

CCA TGG GAA CAA ATG CAT GGC TGG GTT GGT GGG AAA GAT GGT GAT   704
Pro Trp Glu Gln Met His Gly Trp Val Gly Gly Lys Asp Gly Asp
125             130                135

TTT GCT CAC TAT GGC TAT CAT GGT TAC TAT GGA TTA GAT TTT ACG   749
Phe Ala His Tyr Gly Tyr His Gly Tyr Tyr Gly Leu Asp Phe Thr
140             145                150

GCT ATG GAT CAG AAT ATG GGT ACA ATT GAT GAA ATG CGT GAA TTT   794
Ala Met Asp Gln Asn Met Gly Thr Ile Asp Glu Met Arg Glu Phe
```

```
                    155           160           165
GTT GAC CTT GCA CAT TCA TTA GGC ATT AGA GTT GTT CTC GAC ATT   839
Val Asp Leu Ala His Ser Leu Gly Ile Arg Val Val Leu Asp Ile
        170           175           180

GTT ATG AAT CAC GTT GGC TAT CCA ACG ATC GTT GAC ATG CAT GAA   884
Val Met Asn His Val Gly Tyr Pro Thr Ile Val Asp Met His Glu
        185           190           195

TTT GGT TTT GGT GAT ACT GGA GGA CTT CCA AGA GAT TGG ACA CCT   929
Phe Gly Phe Gly Asp Thr Gly Gly Leu Pro Arg Asp Trp Thr Pro
        200           205           210

AAT CAA GCA CAG GGC CAA AAT TGG CAT ACA CAT AAT GAC ATT ATG   974
Asn Gln Ala Gln Gly Gln Asn Trp His Thr His Asn Asp Ile Met
        215           220           225

AAT AAA GAC AAT GAA GCA GCT TGG GCG AAT TGG TGG GGA AGT GAC  1019
Asn Lys Asp Asn Glu Ala Ala Trp Ala Asn Trp Trp Gly Ser Asp
        230           235           240

TGG ATT CGT GCC GAT GAA ACA GCC GGG TAT GAC AAT TGT GGT GGC  1064
Trp Ile Arg Ala Asp Glu Thr Ala Gly Tyr Asp Asn Cys Gly Gly
        245           250           255

AGC GAA CAG ACA ATG TGT ATA GGG TTC TTA CCA GAT ATT AAA ACG  1109
Ser Glu Gln Thr Met Cys Ile Gly Phe Leu Pro Asp Ile Lys Thr
        260           265           270

GAA GTA ACC ACA GGT GTT GAT TTA CCA CCG ATA TTG AGA AAC AAG  1154
Glu Val Thr Thr Gly Val Asp Leu Pro Pro Ile Leu Arg Asn Lys
        275           280           285

TGG AAT GAT CAA GCT AGT GGC TAT GAA GAT TGG TTT GTT CCA GCA  1199
Trp Asn Asp Gln Ala Ser Gly Tyr Glu Asp Trp Phe Val Pro Ala
        290           295           300

GCT GAA CCT TAT CGT CAA GAT TTA AAC ATT GCT CCG AAA GAT TAT  1244
Ala Glu Pro Tyr Arg Gln Asp Leu Asn Ile Ala Pro Lys Asp Tyr
        305           310           315

TTG ATC AAA TGG ATT ACT TCA TGG GTT GAG GAA TTC GGT ATT GAT  1289
Leu Ile Lys Trp Ile Thr Ser Trp Val Glu Glu Phe Gly Ile Asp
        320           325           330

GGA TTC CGT GTT GAT ACA GCA AAG CAT GTA GAG ATT GAG CGA TGG  1334
Gly Phe Arg Val Asp Thr Ala Lys His Val Glu Ile Glu Arg Trp
        335           340           345

GCT GAA TTG AAG AAT GAA GCG GAA GTA GCA CTT CAA ACA TGG CGA  1379
Ala Glu Leu Lys Asn Glu Ala Glu Val Ala Leu Gln Thr Trp Arg
        350           355           360

GAA AAT AAC CCA GAT AAG CCC GGT GCT AAT TGG GAT GAT AAT TTC  1424
Glu Asn Asn Pro Asp Lys Pro Gly Ala Asn Trp Asp Asp Asn Phe
        365           370           375

TGG ATG ACA GCA GAA GTA TTT GGA CAT GGT CTT GGG AAA AGC GAG  1469
Trp Met Thr Ala Glu Val Phe Gly His Gly Leu Gly Lys Ser Glu
        380           385           390

TAT TTT GAT TTT GGT TTC GAT TCT GTG ATT AAT TTT GAA TTC CAG  1514
Tyr Phe Asp Phe Gly Phe Asp Ser Val Ile Asn Phe Glu Phe Gln
        395           400           405

AAT GCA AAC TTC AAT AAT TTA GAA GGT TTA TTT TCT AGA TAT GCA  1559
Asn Ala Asn Phe Asn Asn Leu Glu Gly Leu Phe Ser Arg Tyr Ala
        410           415           420

AAT TCA ATT AAC ACT GAC CCT GAT TTC AAC ATG TTA AGT TAT GTT  1604
Asn Ser Ile Asn Thr Asp Pro Asp Phe Asn Met Leu Ser Tyr Val
        425           430           435

TCA TCT CAT GAT ACA AAG CTT TAT AGT AGA GAT GAC CTT ATT CAG  1649
Ser Ser His Asp Thr Lys Leu Tyr Ser Arg Asp Asp Leu Ile Gln
        440           445           450

GCA GGT ACA GCA TTA CTA TTA CTT CCA GGT GGC GTT CAA GTG TTT  1694
Ala Gly Thr Ala Leu Leu Leu Leu Pro Gly Gly Val Gln Val Phe
        455           460           465
```

```
TAT GGC GAT GAA ACA GCT CGA CCA TTA GGG GAT GGT GGT TCT GAT   1739
Tyr Gly Asp Glu Thr Ala Arg Pro Leu Gly Asp Gly Gly Ser Asp
    470         475         480

CCT GAG CAA GGT ACG CGT TCA TCG ATG AAT TGG GCT AAT ATT AAT   1784
Pro Glu Gln Gly Thr Arg Ser Ser Met Asn Trp Ala Asn Ile Asn
    485         490         495

CAG AAT GTA CTC TCT CAT TGG CAA AAA CTT GGT CAA TTC AGA AAT   1829
Gln Asn Val Leu Ser His Trp Gln Lys Leu Gly Gln Phe Arg Asn
    500         505         510

AAT CAC ATA GCT ATT GGT GCG GGA GCG CAT CAG AAG TTA TCT GAT   1874
Asn His Ile Ala Ile Gly Ala Gly Ala His Gln Lys Leu Ser Asp
    515         520         525

AGT CCG TAT ACG TTT GCG CGT ACG TAT GAA TCA GAC GAT ATA GTT   1919
Ser Pro Tyr Thr Phe Ala Arg Thr Tyr Glu Ser Asp Asp Ile Val
    530         535         540

GAT GAA GTC GTC GTT GCA ACT GGG GCC CAA GGA ACA ACA GCT GTT   1964
Asp Glu Val Val Val Ala Thr Gly Ala Gln Gly Thr Thr Ala Val
    545         550         555

ACT GTA GAA GGT GTT TTT GAA GAT GGG ACA GTT GTT CGA GAT GCT   2009
Thr Val Glu Gly Val Phe Glu Asp Gly Thr Val Val Arg Asp Ala
    560         565         570

TAT ACT GGT GAT GAG ACA ACA GTA ACT AAA GGG ACA GCA ACA TTT   2054
Tyr Thr Gly Asp Glu Thr Thr Val Thr Lys Gly Thr Ala Thr Phe
    575         580         585

ACT GCT GGA ACA CAA GGT ATT ATT CTA ATC GAA AAT ACA GCT GAG   2099
Thr Ala Gly Thr Gln Gly Ile Ile Leu Ile Glu Asn Thr Ala Glu
    590         595         600

CCA GTT ACT AAT TTG CCG ATC GTT TCA GCA ACA CCT GGT AAT AGT   2144
Pro Val Thr Asn Leu Pro Ile Val Ser Ala Thr Pro Gly Asn Ser
    605         610         615

TCT TTT AGG ACA GAT GAC ATA ACA ATC ACG CTA AAT GTT GAT CGA   2189
Ser Phe Arg Thr Asp Asp Ile Thr Ile Thr Leu Asn Val Asp Arg
    620         625         630

GCG GAT ATG GGG AAG TAT ACA CTT GAT GGA AGT GAT CCA GCA GAT   2234
Ala Asp Met Gly Lys Tyr Thr Leu Asp Gly Ser Asp Pro Ala Asp
    635         640         645

GGC CTA ACG TTT ATG GAT GGA GAA GAA ATT GTC ATT GGT GCT GAT   2279
Gly Leu Thr Phe Met Asp Gly Glu Glu Ile Val Ile Gly Ala Asp
    650         655         660

ATG GAG TTT GAT GAA ACA GCA ACA TTG AGA CTC TAT GCA GAA AAT   2324
Met Glu Phe Asp Glu Thr Ala Thr Leu Arg Leu Tyr Ala Glu Asn
    665         670         675

GAA AAT GGC ATA AGA ACA AGG AGT TAC ACA TAT AGG AAG GTA GAT   2369
Glu Asn Gly Ile Arg Thr Arg Ser Tyr Thr Tyr Arg Lys Val Asp
    680         685         690

CCA GAT GCG TTA CTT GAA GTA TAT TTT AAG AAA CCA GCG GAT TGG   2414
Pro Asp Ala Leu Leu Glu Val Tyr Phe Lys Lys Pro Ala Asp Trp
    695         700         705

GGA ACA CCA CAT ATA TAT TAC TAT GAT ACA TTT CCA GAG GAG CCG   2459
Gly Thr Pro His Ile Tyr Tyr Tyr Asp Thr Phe Pro Glu Glu Pro
    710         715         720

GAA GTC ACT TGG ACT ACA GCT CCA GAG ATG ACA TTA GTA GAG GAT   2504
Glu Val Thr Trp Thr Thr Ala Pro Glu Met Thr Leu Val Glu Asp
    725         730         735

GAT TGG TAT GTA TAT GTT TTT GAA AAT GCT GAA AGT GCC AAT ATA   2549
Asp Trp Tyr Val Tyr Val Phe Glu Asn Ala Glu Ser Ala Asn Ile
    740         745         750

ATA TTT AAG GAT TCT TCA GGA AAA CAA ATT CCA GGT CCA AAT GAA   2594
Ile Phe Lys Asp Ser Ser Gly Lys Gln Ile Pro Gly Pro Asn Glu
    755         760         765

CCA GGA TTC TTC ATT GAT CAG ATT GGT TGG TAC GAT GGC GTA AAG   2639
Pro Gly Phe Phe Ile Asp Gln Ile Gly Trp Tyr Asp Gly Val Lys
```

-continued

```
        770         775         780
TGG CTT GAT TCA GAT CCT TTT GAA AGG GAA CCT AAA GAG CCT GCG   2684
Trp Leu Asp Ser Asp Pro Phe Glu Arg Glu Pro Lys Glu Pro Ala
        785         790         795

ACA ACA CCT AAG AAC CTA AGT GTT GTT AAT GTA ACT GAA ACT ACT   2729
Thr Thr Pro Lys Asn Leu Ser Val Val Asn Val Thr Glu Thr Thr
        800         805         810

GTA ACA TTT GAG TGG GAC CAA TCT GAT GGT TAT GTC GTT GAA TAC   2774
Val Thr Phe Glu Trp Asp Gln Ser Asp Gly Tyr Val Val Glu Tyr
        815         820         825

GAG ATT TTA CGT GAT GAG GAT GTT GTT GCT TCA ACT ATT CGT ACA   2819
Glu Ile Leu Arg Asp Glu Asp Val Val Ala Ser Thr Ile Arg Thr
        830         835         840

ACA TTT ACG GAT GAA GAC CTT AAT CCA GAT ACA ACC TAC ACT TAT   2864
Thr Phe Thr Asp Glu Asp Leu Asn Pro Asp Thr Thr Tyr Thr Tyr
        845         850         855

TCT GTC GTA GCT GTT GGA GAA GGC GGG CAG AAA TCC GCC CCA AGT   2909
Ser Val Val Ala Val Gly Glu Gly Gly Gln Lys Ser Ala Pro Ser
        860         865         870

GAA GCG TTA AAA GTG ACT ACA TTA GAA GAA AAT GAT GAA CCT AAG   2954
Glu Ala Leu Lys Val Thr Thr Leu Glu Glu Asn Asp Glu Pro Lys
        875         880         885

GAA CCG GCT GAG GCG CCA GAA AAT TTA CGT ATA GCT GAT ATA ACA   2999
Glu Pro Ala Glu Ala Pro Glu Asn Leu Arg Ile Ala Asp Ile Thr
        890         895         900

GAT ACA ACA GTT ACA ATC AAC TGG AAT GCA TCT AAT GGT TAC GTA   3044
Asp Thr Thr Val Thr Ile Asn Trp Asn Ala Ser Asn Gly Tyr Val
        905         910         915

ACA GGA TAT GAG GTT CTG CGT GAT GGT GTG GTT ATT GGC GAA ACA   3089
Thr Gly Tyr Glu Val Leu Arg Asp Gly Val Val Ile Gly Glu Thr
        920         925         930

ACA CGG ACA ACA TTC ATA GAT ACT GGA TTA GAT GCT GAT AGG ACC   3134
Thr Arg Thr Thr Phe Ile Asp Thr Gly Leu Asp Ala Asp Arg Thr
        935         940         945

TAT ACG TAT ACG ATT GTT GCT CTC GGA GAT GGC GGG CAA AAG TCT   3179
Tyr Thr Tyr Thr Ile Val Ala Leu Gly Asp Gly Gly Gln Lys Ser
        950         955         960

GAT CCG AGC GAA GCG TTA GAA GTA ACA ACT CAA GAA AAA CCA GAA   3224
Asp Pro Ser Glu Ala Leu Glu Val Thr Thr Gln Glu Lys Pro Glu
        965         970         975

GGA AAT CTA GTA ACA ATA TAC TAT AAA AAA GGC TTT GAT ACC CCA   3269
Gly Asn Leu Val Thr Ile Tyr Tyr Lys Lys Gly Phe Asp Thr Pro
        980         985         990

TAT ATG CAT TAT CGT CCG GAA GGT GGA GAG TGG ACG ATC GTT CCA   3314
Tyr Met His Tyr Arg Pro Glu Gly Gly Glu Trp Thr Ile Val Pro
        995         1000        1005

GGA ATT AGA ATG GAA GAA TCA GAA ATA GCA GGC TAT AGT AAG TTA   3359
Gly Ile Arg Met Glu Glu Ser Glu Ile Ala Gly Tyr Ser Lys Leu
        1010        1015        1020

ACC GTT GAT ATT CGG GAA GCA AGC AAG TTG GAA GTA GCC TTT AAT   3404
Thr Val Asp Ile Arg Glu Ala Ser Lys Leu Glu Val Ala Phe Asn
        1025        1030        1035

AAT GGA CGT GGG GCT TGG GAT AGT GAT CAA GAG AAT AAT TAT TTA   3449
Asn Gly Arg Gly Ala Trp Asp Ser Asp Gln Glu Asn Asn Tyr Leu
        1040        1045        1050

TTT GAG CCA GGT GTT CAT ACG TAC ATT CCG AGT CAT GAA GGA AGA   3494
Phe Glu Pro Gly Val His Thr Tyr Ile Pro Ser His Glu Gly Arg
        1055        1060        1065

GGA GAG ATT ATT CCA GGT AAA CCA GGA GCA CCA ATC GAT GGT AAT   3539
Gly Glu Ile Ile Pro Gly Lys Pro Gly Ala Pro Ile Asp Gly Asn
        1070        1075        1080
```

```
AAA GTG ACG ATT TAC TAT CAA AAT GGC TTT GAT ACG CCG TAT GTT   3584
Lys Val Thr Ile Tyr Tyr Gln Asn Gly Phe Asp Thr Pro Tyr Val
    1085        1090        1095

CAT TAC CGC CCA GAA GGC GGA AAT TGG ACC AAC GCC CCA GGA TTA   3629
His Tyr Arg Pro Glu Gly Gly Asn Trp Thr Asn Ala Pro Gly Leu
    1100        1105        1110

AAA ATG GAA GAT TCA GAG TTT GCA AGT TAT AGT AGG TTA ACG CTT   3674
Lys Met Glu Asp Ser Glu Phe Ala Ser Tyr Ser Arg Leu Thr Leu
    1115        1120        1125

GAT ATT GGT GAA GCT AAT CGT GCA GAA GTG GCT TTC AAT AAC GGA   3719
Asp Ile Gly Glu Ala Asn Arg Ala Glu Val Ala Phe Asn Asn Gly
    1130        1135        1140

CGC GGC CTT TGG GAT AGT GAT AAT GAA AAT AAT TAT TTC TTC AAT   3764
Arg Gly Leu Trp Asp Ser Asp Asn Glu Asn Asn Tyr Phe Phe Asn
    1145        1150        1155

ATT GGC GAT AAC ACT TAT ATA CCA GGA AAA AAC GGT TCA GCT GGA   3809
Ile Gly Asp Asn Thr Tyr Ile Pro Gly Lys Asn Gly Ser Ala Gly
    1160        1165        1170

GAG ATT TAT GGA GGT AAG CCA AGA CCA CCA TTA GTA GGA AAT GAA   3854
Glu Ile Tyr Gly Gly Lys Pro Arg Pro Pro Leu Val Gly Asn Glu
    1175        1180        1185

GTA ATC ATT TAT TAT AAA AAT GGT TTT GAT ACA CCG TAT GTT CAT   3899
Val Ile Ile Tyr Tyr Lys Asn Gly Phe Asp Thr Pro Tyr Val His
    1190        1195        1200

TAT CGT CCA GAA GGT GGT ACG TGG ACA AAT GCA CCA GGA ATA AAA   3944
Tyr Arg Pro Glu Gly Gly Thr Trp Thr Asn Ala Pro Gly Ile Lys
    1205        1210        1215

ATG GAT AAG TCA GAA ATA GCA GGT TAC AGT AAA ATA ACG CTT GAT   3989
Met Asp Lys Ser Glu Ile Ala Gly Tyr Ser Lys Ile Thr Leu Asp
    1220        1225        1230

ATT GGT CGC GCA GAT CGA GTA GAA GTA GCC TTT AAT GAC GGT CGT   4034
Ile Gly Arg Ala Asp Arg Val Glu Val Ala Phe Asn Asp Gly Arg
    1235        1240        1245

GGT GCA TGG GAT AGT GAT AAC GAA CGT AAT TAT CTC TTT GTA GTC   4079
Gly Ala Trp Asp Ser Asp Asn Glu Arg Asn Tyr Leu Phe Val Val
    1250        1255        1260

GGT AAC AAT ACT TAT GAA CCA GGA ATT AAC GGC GCA CCT GGT CAG   4124
Gly Asn Asn Thr Tyr Glu Pro Gly Ile Asn Gly Ala Pro Gly Gln
    1265        1270        1275

GTG AAA CAT GGC GTG TTA CCT GAT GAT GGA GAA GAT CCG GGA GAT   4169
Val Lys His Gly Val Leu Pro Asp Asp Gly Glu Asp Pro Gly Asp
    1280        1285        1290

ATT GAA GAC CCT GAT CAT ACC TCC CCT TCA AAG CCG ACT GAT TTA   4214
Ile Glu Asp Pro Asp His Thr Ser Pro Ser Lys Pro Thr Asp Leu
    1295        1300        1305

ACA GCA ATA GCT ACT GCT CAT ACT GTT TCA TTA AGC TGG ACA GCT   4259
Thr Ala Ile Ala Thr Ala His Thr Val Ser Leu Ser Trp Thr Ala
    1310        1315        1320

TCA GCA GAC GAT GTA GAA GTA GCT GGG TAC AAA ATT TAT CGA GAT   4304
Ser Ala Asp Asp Val Glu Val Ala Gly Tyr Lys Ile Tyr Arg Asp
    1325        1330        1335

GGT GTG GAA ATC GGT GTT ACT GAA TCA ACA ACT TAT ACG GAT TCA   4349
Gly Val Glu Ile Gly Val Thr Glu Ser Thr Thr Tyr Thr Asp Ser
    1340        1345        1350

GGC TTA ACG GCA GAA ACA ACG TAT AGC TAT ATG GTA CAA GCT TAT   4394
Gly Leu Thr Ala Glu Thr Thr Tyr Ser Tyr Met Val Gln Ala Tyr
    1355        1360        1365

GAT ACT TCT AAT AAT TTC TCG GCA TTA AGT GAT GAA CTG ACA ATT   4439
Asp Thr Ser Asn Asn Phe Ser Ala Leu Ser Asp Glu Leu Thr Ile
    1370        1375        1380

GAA ACC GCC GAG AAA ACG GGT GTT GAT CCA GGA GGG GAT ATG CCT   4484
Glu Thr Ala Glu Lys Thr Gly Val Asp Pro Gly Gly Asp Met Pro
```

```
                    1385            1390            1395

TAT  TCC  ACG  AAT  CCA  TCG  TTT  GGT  AAG  AAG  GTA  ACA  ACG  CCA  ATC    4529
Tyr  Ser  Thr  Asn  Pro  Ser  Phe  Gly  Lys  Lys  Val  Thr  Thr  Pro  Ile
     1400           1405           1410

ACA  ATT  GAT  GGT  GTT  AAT  GAC  GGG  GAA  TGG  ACA  GAT  GAT  ATG  TTG    4574
Thr  Ile  Asp  Gly  Val  Asn  Asp  Gly  Glu  Trp  Thr  Asp  Asp  Met  Leu
     1415           1420           1425

ATT  GCA  ATT  GGT  ATG  GCT  GGT  GAC  GAC  CCA  CGT  TCG  CTC  GGG  GAC    4619
Ile  Ala  Ile  Gly  Met  Ala  Gly  Asp  Asp  Pro  Arg  Ser  Leu  Gly  Asp
     1430           1435           1440

AAT  TGG  TCT  ATG  CAT  GAA  ACA  CCA  ATG  GAC  CTT  ACT  CAC  CTA  TGG    4664
Asn  Trp  Ser  Met  His  Glu  Thr  Pro  Met  Asp  Leu  Thr  His  Leu  Trp
     1445           1450           1455

GGA  GCA  TGG  GAC  CAT  GAG  TAC  TTG  TAT  CTT  GCT  TGG  CAA  TAT  GTA    4709
Gly  Ala  Trp  Asp  His  Glu  Tyr  Leu  Tyr  Leu  Ala  Trp  Gln  Tyr  Val
     1460           1465           1470

GAT  GTA  ACA  GAT  ATT  ATT  GAC  CCA  GCT  AAC  GCA  GGC  TCA  TCA  GCT    4754
Asp  Val  Thr  Asp  Ile  Ile  Asp  Pro  Ala  Asn  Ala  Gly  Ser  Ser  Ala
     1475           1480           1485

GGT  ACC  ACA  ATT  AGC  CAG  ATG  GAT  ATG  CCA  CAA  ACC  ATT  GCA  ATT    4799
Gly  Thr  Thr  Ile  Ser  Gln  Met  Asp  Met  Pro  Gln  Thr  Ile  Ala  Ile
     1490           1495           1500

GAT  ACC  ATC  CCA  GAG  CAA  GGT  GCA  ACA  CAT  GAT  ATG  TGG  GGG  AAA    4844
Asp  Thr  Ile  Pro  Glu  Gln  Gly  Ala  Thr  His  Asp  Met  Trp  Gly  Lys
     1505           1510           1515

AAT  GGT  GGT  GAA  TCA  CTT  TGG  GGA  GGA  CCA  GAT  TTA  CCT  GAT  TAC    4889
Asn  Gly  Gly  Glu  Ser  Leu  Trp  Gly  Gly  Pro  Asp  Leu  Pro  Asp  Tyr
     1520           1525           1530

CAA  CTA  AAT  ATC  GCA  TCT  AAT  ATG  TTC  CAT  TCA  GGC  TAT  ATT  TCT    4934
Gln  Leu  Asn  Ile  Ala  Ser  Asn  Met  Phe  His  Ser  Gly  Tyr  Ile  Ser
     1535           1540           1545

AGA  GCA  GTT  GAT  GGT  GTA  TTT  CCT  GTT  GAC  GAT  GGA  GGA  ATA  AAT    4979
Arg  Ala  Val  Asp  Gly  Val  Phe  Pro  Val  Asp  Asp  Gly  Gly  Ile  Asn
     1550           1555           1560

TAT  AAA  ACG  GGT  GAG  GAA  GCA  GGA  ATT  ACA  GTA  AAG  TTT  TCT  AAA    5024
Tyr  Lys  Thr  Gly  Glu  Glu  Ala  Gly  Ile  Thr  Val  Lys  Phe  Ser  Lys
     1565           1570           1575

GGT  AAA  GGG  TAT  TCA  ACA  TTG  TGG  GGG  GTG  TTA  GAT  GCT  GAT  GAT    5069
Gly  Lys  Gly  Tyr  Ser  Thr  Leu  Trp  Gly  Val  Leu  Asp  Ala  Asp  Asp
     1580           1585           1590

GCA  GTT  GAT  CCT  AGT  AAA  CTT  GTG  AAC  TTC  ACC  GAG  CTT  GCC  CAT    5114
Ala  Val  Asp  Pro  Ser  Lys  Leu  Val  Asn  Phe  Thr  Glu  Leu  Ala  His
     1595           1600           1605

GAT  TCA  ACA  CGA  GAT  ACT  TTT  TAT  GAA  GCA  AAG  ATT  CCT  TTA  GCT    5159
Asp  Ser  Thr  Arg  Asp  Thr  Phe  Tyr  Glu  Ala  Lys  Ile  Pro  Leu  Ala
     1610           1615           1620

GCA  ATT  GGT  AAT  CCC  GAC  ATT  GAA  AAT  GAA  CGC  ATT  GGT  GTC  ATG    5204
Ala  Ile  Gly  Asn  Pro  Asp  Ile  Glu  Asn  Glu  Arg  Ile  Gly  Val  Met
     1625           1630           1635

ATT  CAT  CAA  GGT  GAA  TTT  TCG  CCG  ATG  GAC  ACG  CTA  CCG  AAT  GAC    5249
Ile  His  Gln  Gly  Glu  Phe  Ser  Pro  Met  Asp  Thr  Leu  Pro  Asn  Asp
     1640           1645           1650

CCC  GCA  ACA  TCC  GAT  ACA  CCA  GGT  GTG  AGT  GAA  TCA  AAT  TCG  CCA    5294
Pro  Ala  Thr  Ser  Asp  Thr  Pro  Gly  Val  Ser  Glu  Ser  Asn  Ser  Pro
     1655           1660           1665

TTA  GAA  TGG  GAA  GAC  ATT  GAC  CTG  TTA  ACA  GTG  CCA  TTT  GCA  AGA    5339
Leu  Glu  Trp  Glu  Asp  Ile  Asp  Leu  Leu  Thr  Val  Pro  Phe  Ala  Arg
     1670           1675           1680

ATT  GGC  CAA  TAA  TTATGAAATA  AGCCGGCATG  AGTCTATGCT                       5381
Ile  Gly  Gln

GGCTTTTTGT  ACGGCTGGCA  GTTGCACATG  CAGAGACGAC  ACTGTGGTGT                   5431
```

```
AACAGCTAGA TGACAGTAAA TCATTGGCAT TCCAGATGGT CGGAATAAAA    5481
GACGGATTTG TGTATATAGT AACTCTATTG ATGAAGTTTT CCCGTTAGTT    5531
CCATCCTCAG ATTATCAATC ATCAATAATA GGTGGTTTCA TGGATTGCTT    5581
AGGAAATATC GAGGATGACC TATTTACTGT TCACTAAATC TGATTAGAGT    5631
TTATTGGTAT CAAAAAGCG TTATTTCTTC AAAGCAAGAA GCAGGCAACT     5681
GGGATTATCT ACATTCCCA ATGATATGAA AAATGCTGTT AAAAAAGATG     5731
GTTGAATATT                                                5741
```